US011832799B2

(12) United States Patent
Huang et al.

(10) Patent No.: US 11,832,799 B2
(45) Date of Patent: Dec. 5, 2023

(54) SURFACE MOUNTED ASSEMBLY AND RELATED ENDOSCOPE

(71) Applicant: ALTEK BIOTECHNOLOGY CORPORATION, Hsinchu (TW)

(72) Inventors: Yu-Cheng Huang, Hsinchu (TW); Fei-Jen Teng, Hsinchu (TW)

(73) Assignee: ALTEK BIOTECHNOLOGY CORPORATION, Hsinchu (TW)

( * ) Notice: Subject to any disclaimer, the term of this patent is extended or adjusted under 35 U.S.C. 154(b) by 240 days.

(21) Appl. No.: 17/409,827

(22) Filed: Aug. 24, 2021

(65) Prior Publication Data

US 2023/0065514 A1   Mar. 2, 2023

(51) Int. Cl.
| H05K 1/18 | (2006.01) |
| A61B 1/05 | (2006.01) |
| A61B 1/00 | (2006.01) |
| A61B 1/06 | (2006.01) |
| H05K 1/11 | (2006.01) |

(52) U.S. Cl.
CPC .......... *A61B 1/05* (2013.01); *A61B 1/00018* (2013.01); *A61B 1/0661* (2013.01); *H05K 1/115* (2013.01); *H05K 1/181* (2013.01); *H05K 2201/10356* (2013.01)

(58) Field of Classification Search
CPC ............ A61B 1/04; A61B 1/05; A61B 1/00114–00119; A61B 1/00133; A61B 1/06; A61B 1/0661; H05K 1/11; H05K 1/115; H05K 1/18; H05K 1/181

USPC ............. 600/117–120; 361/760–763, 767, 361/792–795; 174/258–261
See application file for complete search history.

(56) References Cited

U.S. PATENT DOCUMENTS

| 6,494,739 B1 | 12/2002 | Vivenzio |
| 8,633,429 B2 | 1/2014 | Eismann |
| 2001/0016679 A1* | 8/2001 | Futatsugi ............ A61B 1/05 600/176 |
| 2004/0176661 A1* | 9/2004 | Futatsugi ........... G02B 23/2484 600/110 |

(Continued)

FOREIGN PATENT DOCUMENTS

| CN | 106646850 A | 5/2017 |
| CN | 110087529 A | 8/2019 |

(Continued)

*Primary Examiner* — Tuan T Dinh
(74) *Attorney, Agent, or Firm* — Winston Hsu

(57) ABSTRACT

A surface mounted assembly is provided and includes a surface mounted device, a cable and a circuit board. The circuit board includes a first outer side and a second outer side opposite to first outer side, and a conductive hole structure. The cable is inserted into the conductive hole structure from the first outer side of the circuit board and affixed with and electrically connected to the conductive hole structure to locate a terminal of the cable between the first outer side and the second outer side of the circuit board. The surface mounted device is mounted on the second outer side of the circuit board. An electrical connecting component of the surface mounted device and the terminal of the cable are affixed with and electrically connected to the conductive hole structure and electrically connected to each other by the conductive hole structure. Furthermore, an endoscope is provided.

14 Claims, 14 Drawing Sheets

(56) References Cited

U.S. PATENT DOCUMENTS

| | | | |
|---|---|---|---|
| 2006/0237223 A1* | 10/2006 | Chen | H05K 1/0218 |
| | | | 174/262 |
| 2012/0104230 A1* | 5/2012 | Eismann | A61B 1/051 |
| | | | 438/66 |
| 2014/0003018 A1* | 1/2014 | Fujimori | H05K 1/181 |
| | | | 29/850 |
| 2016/0029879 A1 | 2/2016 | Ishikawa | |
| 2017/0251914 A1 | 9/2017 | Kitano | |
| 2020/0194951 A1* | 6/2020 | Loo | H05K 3/3405 |
| 2020/0196434 A1 | 6/2020 | Kuo | |
| 2020/0221598 A1 | 7/2020 | Loo | |
| 2021/0068617 A1* | 3/2021 | Liou | H01P 3/12 |
| 2021/0068641 A1 | 3/2021 | Sørensen | |

FOREIGN PATENT DOCUMENTS

| | | |
|---|---|---|
| CN | 106886089 B | 6/2020 |
| CN | 112054322 A | 12/2020 |
| EP | 1 455 216 A1 | 9/2004 |
| JP | 4578913 B2 | 11/2010 |
| TW | M603741 U | 11/2020 |

\* cited by examiner

SURFACE MOUNTED ASSEMBLY AND RELATED ENDOSCOPE

BACKGROUND OF THE INVENTION

1. Field of the Invention

The present invention related to a surface mounted assembly and a related endoscope, and more specifically, to a surface mounted assembly with compact structure and small size and a related endoscope.

2. Description of the Prior Art

An endoscopy is a medical procedure in which an endoscope is inserted into a patient's body to allow a surgeon to inspect an interior of the patient's body. The endoscopy has gained broad acceptance because it only needs a small incision for insertion of the endoscope. However, since the conventional endoscope still has a bulky image capturing assembly, a size of the incision cannot be further reduced in order for insertion of the endoscope with such a bulky image capturing assembly. Therefore, an improvement is required.

SUMMARY OF THE INVENTION

It is an objective of the present invention to provide a surface mounted assembly and a related endoscope for solving the aforementioned problems.

In order to achieve the aforementioned objective, the present invention discloses a surface mounted assembly. The surface mounted assembly includes a surface mounted device, at least one cable and a circuit board. The surface mounted device includes at least one electrical connecting component. The circuit board includes a first outer side, a second outer side opposite to the first outer side, and at least one conductive hole structure. The at least one cable is inserted into the at least one conductive hole structure from the first outer side of the circuit board. A terminal of the at least one cable is located between the first outer side and the second outer side of the circuit board. The surface mounted device is mounted on the second outer side of the circuit board. The terminal of at least one cable and the at least one electrical connecting component of the surface mounted device are affixed with and electrically connected to the at least one conductive hole structure, and the at least one electrical connecting component of the surface mounted device is electrically connected to the terminal of the at least one cable by the at least one conductive hole structure.

In order to achieve the aforementioned objective, the present invention further discloses an endoscope. The endoscope includes the aforementioned surface mounted assembly and a lens assembly. The surface mounted device of the surface mounted assembly is an image sensing device. The lens assembly is assembled with the surface mounted device.

In summary, the present invention utilizes the conductive hole structure to be affixed with and electrically connected to the electrical connecting component of the surface mounted device and the terminal of the cable, so that the electrical connecting component of the surface mounted device can be electrically connected to the terminal of the cable by the conductive hole structure. The aforementioned configuration of the present invention is space-saving. Therefore, the present invention has advantages of compact structure and small size.

These and other objectives of the present invention will no doubt become obvious to those of ordinary skill in the art after reading the following detailed description of the preferred embodiment that is illustrated in the various figures and drawings.

DETAILED DESCRIPTION

In the following detailed description of the preferred embodiments, reference is made to the accompanying drawings which form a part hereof, and in which is shown by way of illustration specific embodiments in which the invention may be practiced. In this regard, directional terminology, such as "top", "bottom", "front", "back", etc., is used with reference to the orientation of the Figure (s) being described. The components of the present invention can be positioned in a number of different orientations. As such, the directional terminology is used for purposes of illustration and is in no way limiting. Accordingly, the drawings and descriptions will be regarded as illustrative in nature and not as restrictive. Also, the term "connect" is intended to mean either an indirect or direct electrical/mechanical connection. Thus, if a first device is connected to a second device, that connection may be through a direct electrical/mechanical connection, or through an indirect electrical/mechanical connection via other devices and connections.

Figure 1:
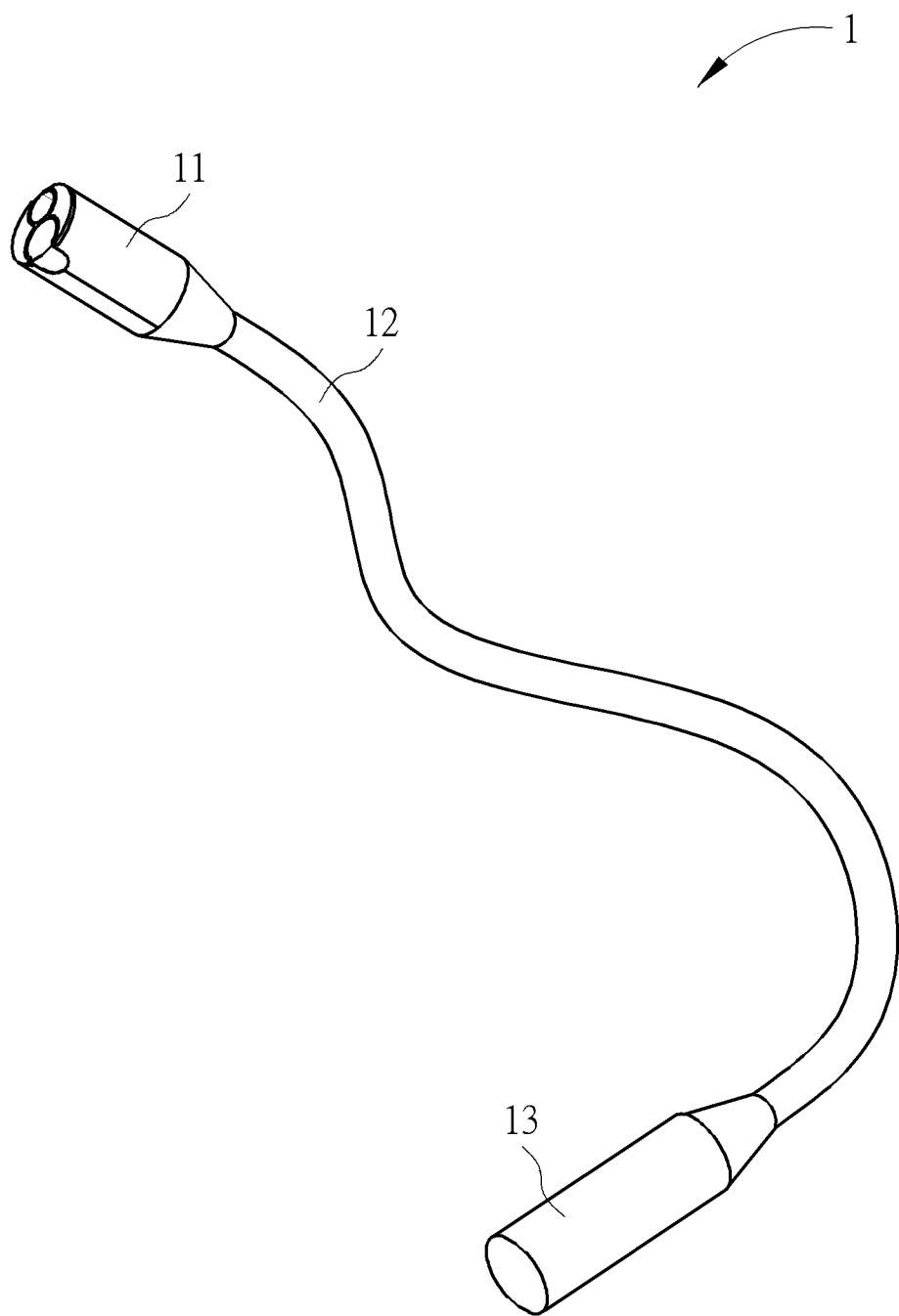
FIG. 1 is a schematic diagram of an endoscope according to a first embodiment of the present invention.

Please refer to FIG. 1. FIG. 1 is a schematic diagram of an endoscope 1 according to an embodiment of the present invention. As shown in FIG. 1, the endoscope 1 includes a surface mounted assembly 11, a flexible tube 12 and a handle 13. The surface mounted assembly 11 is an image sensing assembly for capturing images. The handle 13 is for hand-holding and can be provided with a control console for at least controlling the surface mounted assembly 11. The flexible tube 12 is connected between the surface mounted assembly 11 and the handle 13.

Figure 2:
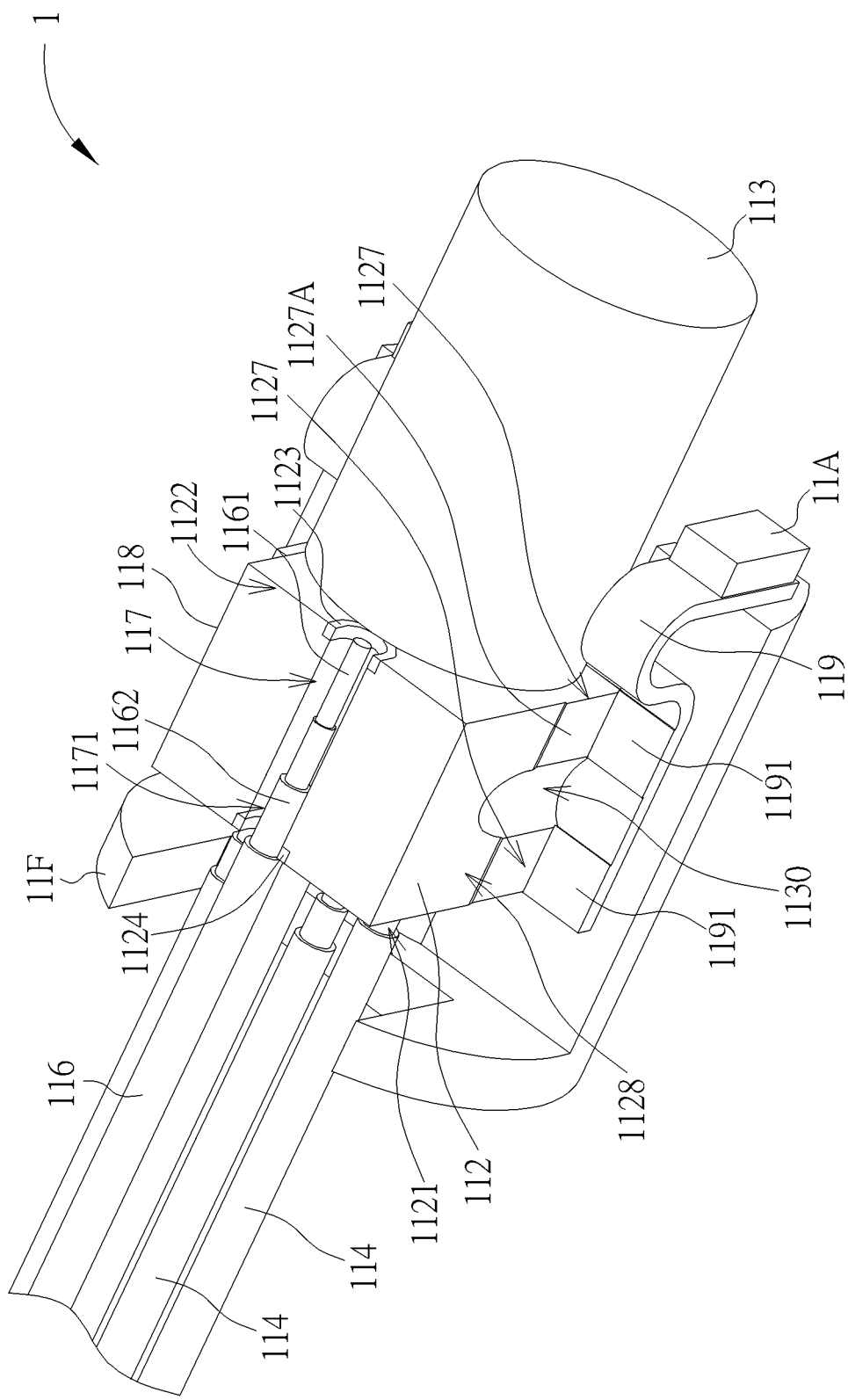
FIG. 2 and FIG. 3 are partial diagrams of the endoscope at different views according to the first embodiment of the present invention.
Figure 3:
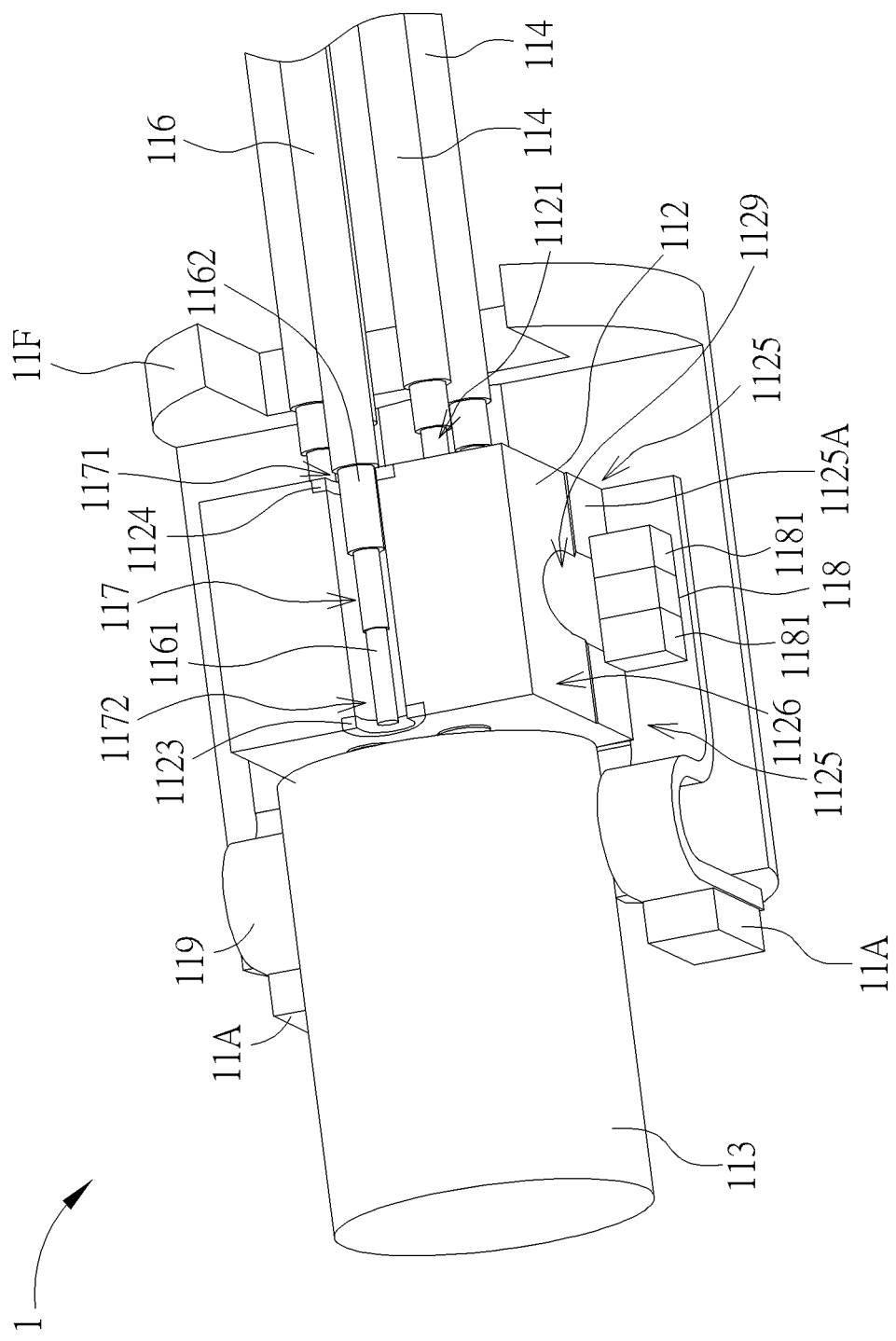

Please refer to FIG. 1 to FIG. 7. FIG. 2 and FIG. 3 are partial diagrams of the endoscope 1 at different views according to the first embodiment of the present invention.

Figure 4:
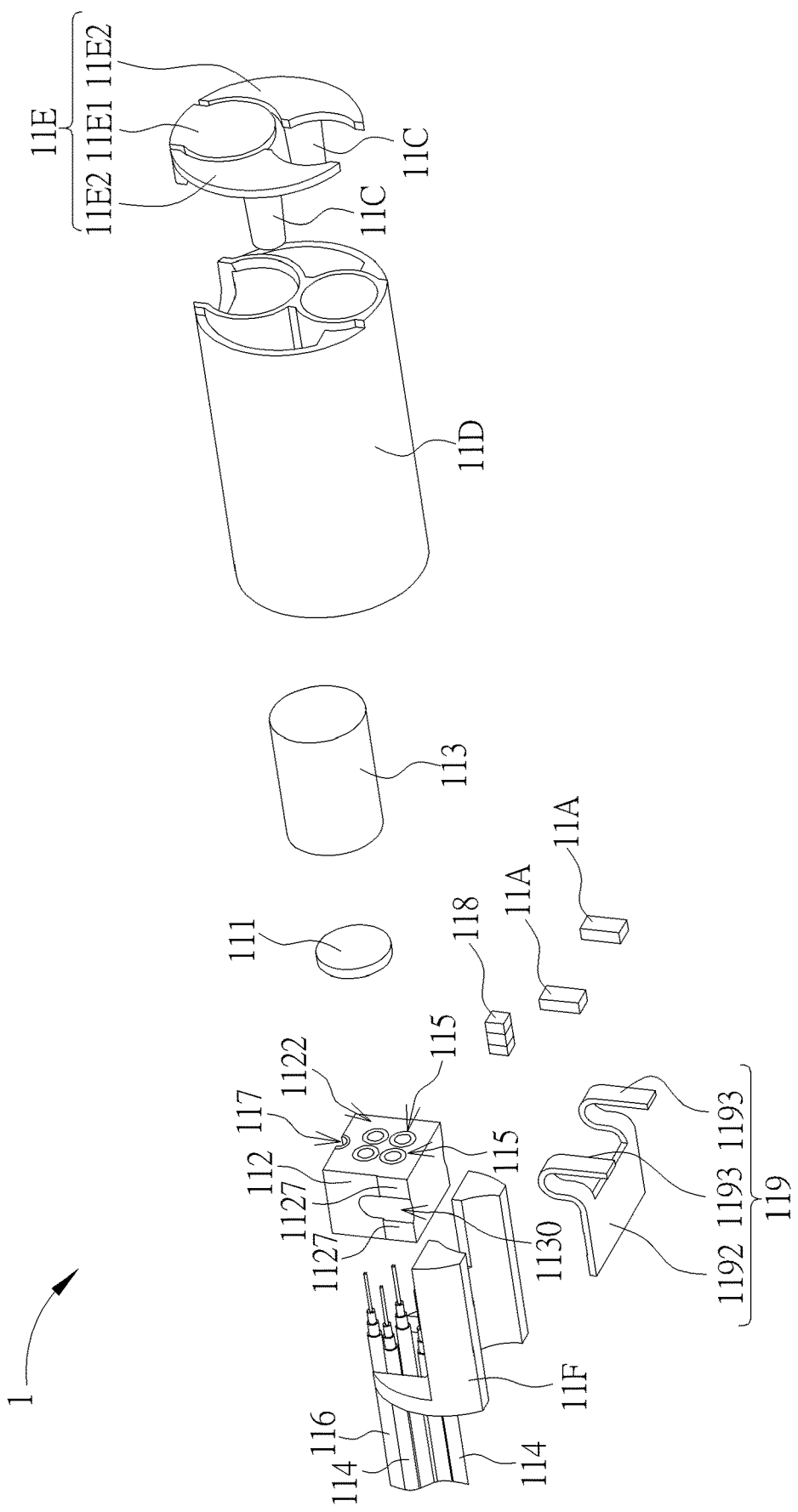
FIGS. 4 and 5 are partial exploded structural diagrams of the endoscope at different views according to the first embodiment of the present invention.
Figure 5:
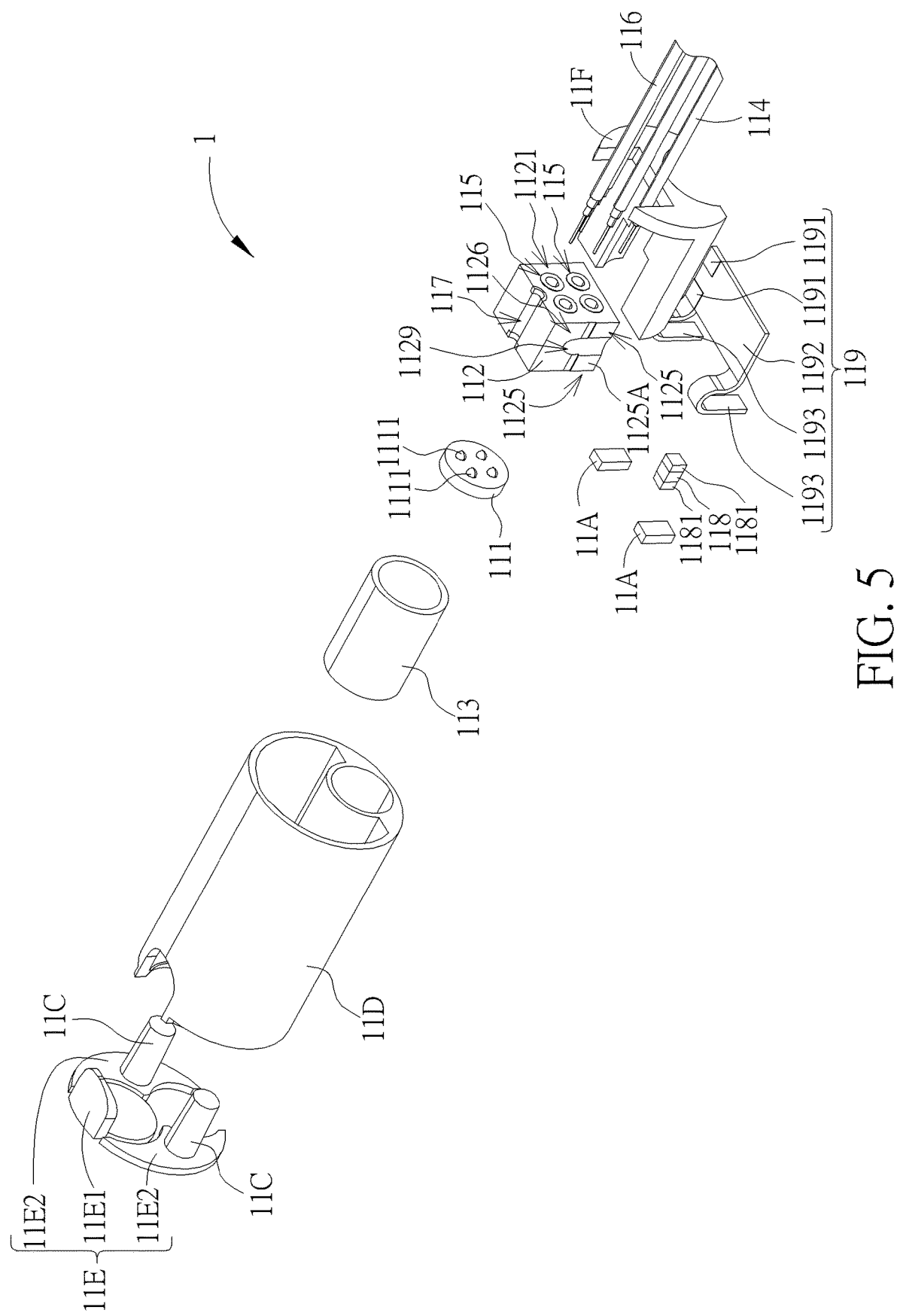
Figure 6:
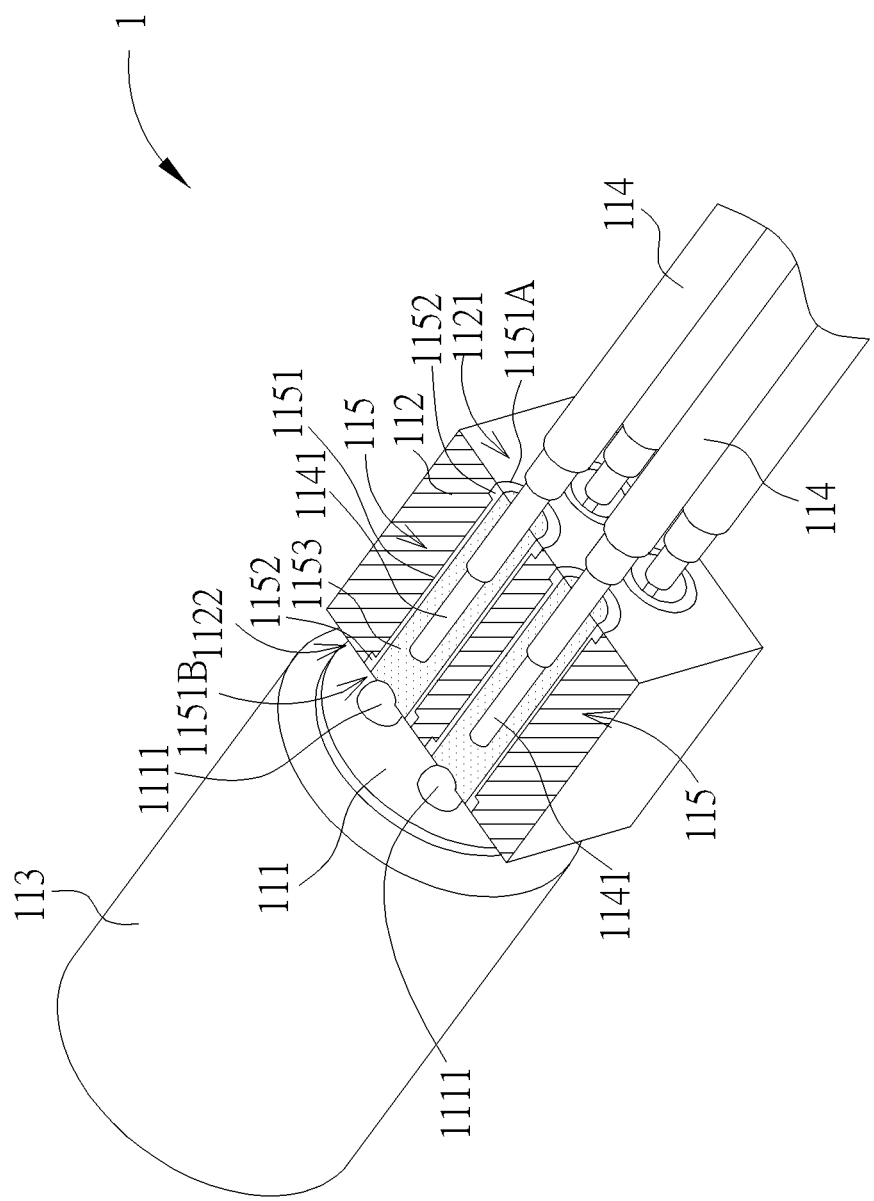
FIG. 6 is a partial internal structural diagram of the endoscope according to the first embodiment of the present invention.
Figure 7:
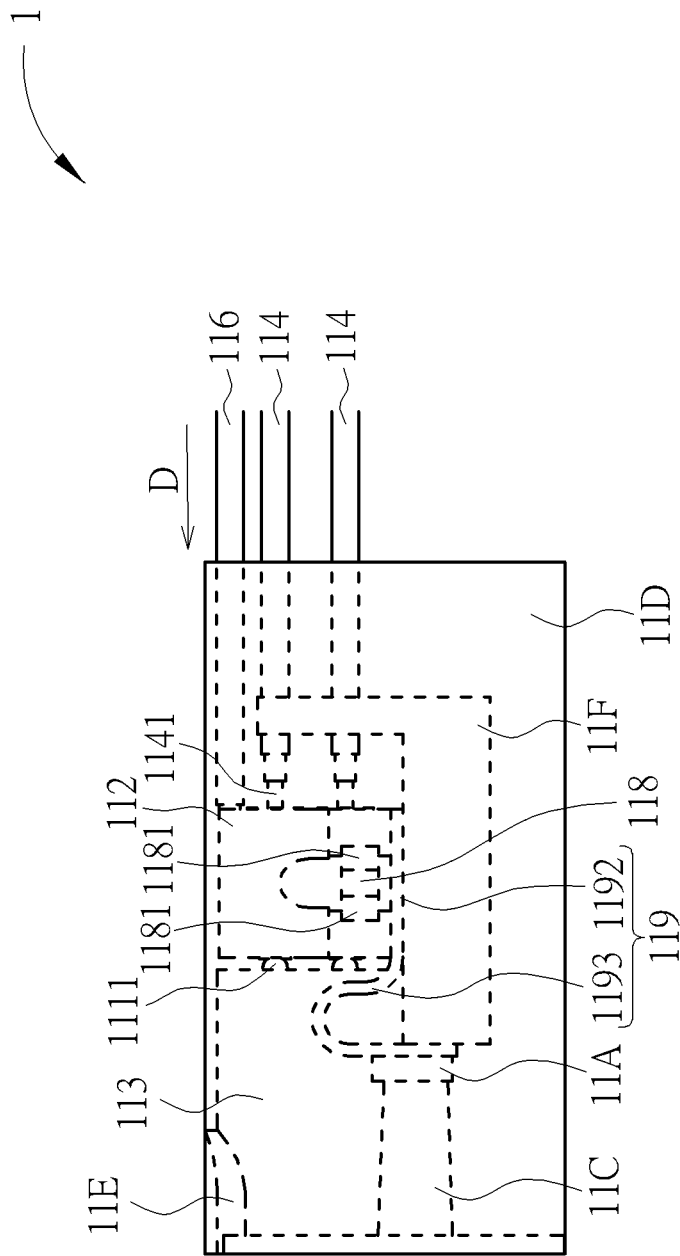
FIG. 7 is a partial lateral view of the endoscope according to the first embodiment of the present invention.

FIGS. 4 and 5 are partial exploded structural diagrams of the endoscope 1 at different views according to the first embodiment of the present invention. FIG. 6 is a partial internal structural diagram of the endoscope 1 according to the first embodiment of the present invention. FIG. 7 is a partial lateral view of the endoscope 1 according to the first embodiment of the present invention. As shown in FIG. 1 to FIG. 7, the surface mounted assembly 11 is located at a distal end of the flexible tube 12 away from the handle 13 and includes a surface mounted device 111, a circuit board 112, a lens assembly 113 and four cables 114. The four cables 114 pass through the flexible tube 12 and electrically connected between the circuit board 112 and a circuit board of the control console of the handle 13, which is not shown in the figures, for providing power and signal transmission between the circuit board 112 and the circuit board of the control console of the handle 13.

In this embodiment, the surface mounted device 111 is an image sensing device, e.g., a CMOS sensor, and includes four electrical connecting components 1111. The circuit board 112 includes a first outer side 1121, a second outer side 1122 opposite to the first outer side 1121, and four conductive hole structures 115. Each of the cables 114 is inserted into the corresponding conductive hole structure 115 from the first outer side 1121 of the circuit board 112. A terminal 1141 of each of the cables 114 is located between the first outer side 1121 and the second outer side 1122 of the circuit board 112 and affixed with and electrically connected to the corresponding conductive hole structure 115. The surface mounted device 111 is mounted on the second outer side 1122 of the circuit board 112. Each of the electrical connecting components 1111 of the surface mounted device 111 is affixed with and electrically connected to the corresponding conductive hole structure 115. Each of the electrical connecting components 1111 of the surface mounted device 111 is electrically connected to the terminal of the corresponding cables 114 by the corresponding conductive hole structure 115. The lens assembly 113 is assembled with the surface mounted device 111 and is a fixed focal length lens assembly or a zoom lens assembly configured to zoom in or zoom out a view of the surface mounted device 111. It should be noted that a terminal of a cable is a conducting part of the cable.

However, the numbers of the electrical connecting component, the conductive hole structure and the cable are not limited to this embodiment. It depends on practical demands. For example, in another embodiment, there can be only one conductive hole structure, one electrical connecting component affixed with and electrically connected to the conductive hole structure, one cable whose terminal is affixed with and electrically connected to the conductive hole structure.

Specifically, the first outer side 1121 and the second outer side 1122 of the circuit board 112 can be substantially perpendicular to an extending direction of each of the cables 114. Each of the conductive hole structures 115 can include a plated through hole 1151 with two ring-shaped pad portions 1152 at two ends and a plating inner wall. Each of the plated through holes 1151 penetrates through the circuit board 112 and has a first opening 1151A formed on the first outer side 1121 of the circuit board 112 and a second opening 1151B formed on the second outer side 1122 of the circuit board 112. Each of the cables 114 can be inserted into the corresponding plated through hole 1151 from the first outer side 1121 of the circuit board 112 via the first opening 1151A of the plated through hole 1151, and each of the plated through holes 1151 can be at least partially filled with an electrically conductive material 1153, so as to establish a mechanical and electrical connection of the terminal of the corresponding cable 114 and the corresponding conductive hole structure 115. Each of the electrical connecting components 1111 can be aligned with the second opening 1151B of the corresponding plated through hole 1151 along the extending direction of the corresponding cable 114 and affixed with a portion of the electrically conductive material 1153 located adjacent to the second opening 1151B of the corresponding plated through hole 1151, so as to establish a mechanical and electrical connection of the corresponding conductive hole structure 115 and the corresponding electrical connecting component 1111. In other words, each of the electrical connecting components 1111 can be aligned with the corresponding cable 114 along the extending direction of the corresponding cable 114.

More specifically, the electrically conductive material 1153 can be a solder material, and each of the electrical connecting components 1111 can be a solder ball which is affixed with and electrically connected to the electrically conductive material 1153 located adjacent to the second opening 1151B of the corresponding plated through hole 1151.

When it is desired to assemble the cables 114, the circuit board 112 and the surface mounted device 111 together, firstly, each of the cables 114 can be inserted into the corresponding plated through hole 1151 respectively to locate the terminal 1141 of each of the cables 114 between the first outer side 1121 and the second outer side 1122 of the circuit board 112, and then the circuit board 112 and the terminals of the cables 114 can be sunken into the melted electrically conductive material 1153 to fill each of the plated through holes 1151 with the electrically conductive material 1153. After each of the plated through holes 1151 is filled with the electrically conductive material 1153, the surface mounted device 111 can be further mounted on the circuit board 112 by surface mounted technology, so that each of the electrical connecting components 1111 can be affixed with and electrically connected to the corresponding electrically conductive material 1153, so as to be electrically connected to the terminal of the corresponding cable 114.

However, the present invention is not limited to this embodiment. For example, in another embodiment, the electrical connecting component can be a protruding pins or a flat pad, and the conductive hole structure can include a plated through hole with one ring-shaped pad portion at one end or without any ring-shaped pad portion thereon and filled with the electrically conductive material. Alternatively, in another embodiment, the first outer side and the second outer side of the circuit board can be substantially inclined relative to the extending direction of each of the cables.

Furthermore, as shown in FIG. 2 to FIG. 7, in this embodiment, the surface mounted assembly 11 further includes an auxiliary cable 116. The circuit board 112 further includes a signal layer 1123 and a ground layer 1124 separated from the signal layer 1123. A half through hole structure 117 is formed on an outer periphery of the circuit board 112. The half through hole structure 117 has a first end portion 1171 adjacent to the first outer side 1121 of the circuit board 112 and a second end portion 1172 adjacent to the second outer side 1122 of the circuit board 112. The signal layer 1123 and the ground layer 1124 are respectively located adjacent to the second end portion 1172 and the first end portion 1171 of the half through hole structure 117 and respectively exposed out of a wall of the second end portion 1172 of the half through hole structure 117 and a wall of the first end portion 1171 of the half through hole structure 117. The auxiliary cable 116 is disposed inside the half through hole structure 117. A terminal 1161 of the auxiliary cable 116 is affixed with and electrically connected to the signal layer 1123, and a shield 1162 of the auxiliary cable 116 is affixed with and electrically connected to the ground layer 1124.

Specifically, the terminal 1161 and the shield 1162 of the auxiliary cable 116 can be affixed with and electrically connected to the signal layer 1123 and the ground layer 1124 respectively by soldering.

However, the present invention is not limited to this embodiment. For example, in another embodiment, the signal layer or the ground layer can be located adjacent to a middle portion of the half through hole structure between the first end portion and the second end portion of the half through hole structure and exposed out of a wall of the middle portion of the half through hole structure. Alternatively, in another embodiment, the signal layer can be located adjacent to the first end portion of the half through hole structure and exposed out of the wall of the first end portion of the half through hole structure. Alternatively, in another embodiment, there can be a plurality of half through hole structures, a plurality of signal layers respectively exposed out of walls of the plurality of half through hole structures, and a plurality of auxiliary cables, and the terminal of each of the auxiliary cables can be affixed with and electrically connected to the corresponding signal layer by soldering. Alternatively, in another embodiment, there can be no half through hole structure and no auxiliary cable as there is no signal layer and no ground layer.

As shown in FIG. 2 to FIG. 7, in this embodiment, the surface mounted assembly 11 further includes a passive electronic component 118, e.g., a capacitor or a resistor, electrically connected to the circuit board 112.

Specifically, the passive electronic component 118 can include two first cooperating contacts 1181. The circuit board 112 can include two first auxiliary contacts 1125. Each of the two first auxiliary contacts 1125 can include a first pad portion 1125A located on a first lateral side 1126 of the circuit board 112 adjacent to and located between the first outer side 1121 and the second outer side 1122 of the circuit board 112. Each of the first cooperating contacts 1181 can be affixed with and electrically connected to the first pad portion 1125A of the corresponding first auxiliary contact 1125 by soldering, so as to establish a mechanical and electrical connection of the corresponding first cooperating contact 1181 and the corresponding first auxiliary contact 1125. Preferably, a recess 1129 can be formed on the first lateral side 1126 of the circuit board 112 and located between the two first pad portions 1125A for facilitating the aforementioned soldering process.

However, the present invention is not limited to this embodiment. For example, in another embodiment, there can be only one first auxiliary contact having one first pad portion exposed out of the first lateral side of the circuit board, and one first cooperating contact electrically connected to and affixed with the first pad portion. Alternatively, in anther embodiment, there can be no recess formed on the first lateral side of the circuit board and located between the two first pad portions. Alternatively, in anther embodiment, there can be no passive electronic component or two passive electronic components located at two opposite lateral sides of the circuit board.

In addition, as shown in FIG. 2 to FIG. 9, in this embodiment, the surface mounted assembly 11 further includes a flexible auxiliary circuit board 119 and two light emitting components 11A. The two light emitting components 11A are disposed on the flexible auxiliary circuit board 119 and configured to emit light. The flexible auxiliary circuit board 119 is affixed with and electrically connected to the circuit board 112.

Specifically, the circuit board 112 can include two second auxiliary contacts 1127. Each of the second auxiliary contacts 1127 can include a second pad portion 1127A. The two second pad portions 1127A can be located on a second lateral side 1128 of the circuit board 112 opposite to the first lateral side 1126 of the circuit board 112. The flexible auxiliary circuit board 119 can include two second cooperating contacts 1191 electrically connected to the two light emitting components 11A and located adjacent to the two second pad portions 1127A. Each of the second cooperating contacts 1191 can include a third pad portion 1191A. Each of the third pad portions 1191A can be perpendicular to and affixed with the second pad portion 1127A by soldering, so as to establish a mechanical and electrical connection of the corresponding second cooperating contact 1191 and the corresponding second auxiliary contact 1127. Preferably, a recess 1130 can be formed on the second lateral side 1128 of the circuit board 112 and located between the two second pad portions 1127A for facilitating the aforementioned soldering process.

However, the present invention is not limited to this embodiment. For example, in another embodiment, the two second pad portions can be located on the first lateral side and the second lateral side of the circuit board respectively. Alternatively, in another embodiment, there can be one flexible auxiliary circuit board and one light emitting component. Alternatively, in another embodiment, there can be no flexible auxiliary circuit board and no light emitting component.

Besides, as shown in FIG. 2 to FIG. 7, the surface mounted assembly 11 further includes two light guiding components 11C, a shell 11D, a window 11E and a mounting base 11F. The two light guiding components 11C are disposed on the shell 11D and configured to guide the light emitted from the two light emitting components 11A. The window 11E is disposed on the shell 11D and configured to protect internal components, such as the lens assembly 113 and the light guiding components 11C, from being damaged. The window 11E includes an objective lens 11E1 and two light guiding lenses 11E2. The objective lens 11E1 is configured to receive light from an observed object and the light from the observed object can pass through the objective lens 11E1 and travel toward the lens assembly 113. The two light guiding lenses 11E2 are connected to the two light guiding components 11C respectively and configured to receive light from the two light guiding components 11C respectively, and the light from the two light guiding components 11C can pass through the two light guiding lenses 11E2 respectively and travel toward the observed object. The mounting base 11F is slidably installed inside the shell 11D for driving at least the circuit board 112, the surface mounted device 111, the lens assembly 113, the flexible auxiliary circuit board 119 and the two light emitting components 11A to slide together with the mounting base 11F.

Specifically, the flexible auxiliary circuit board 119 can include a main body 1192 and two resilient arms 1193 extending from the main body 1192. The two light emitting components 11A can be disposed on the two resilient arms 1193. The mounting base 11F can be adhered with the two resilient arms 1193 by adhesives, e.g., UV glue. Each of resilient arms 1193 is configured to bias the light emitting components 11A to abut against the corresponding light guiding component 11C. The flexible auxiliary circuit board 119 can be located between and abutted by a flat abutting structure of the mounting base 11F and a flat abutting structure of the circuit board 112.

However, the present invention is not limited to this embodiment. For example, in another embodiment, there can be a plurality of supporting structures formed on the mounting base, and one light guiding component disposed on the shell.

As shown in FIG. 2 to FIG. 7, during assembly of the surface mounted assembly 11, the mounting base 11F can be pushed to slide into the shell 11D along a sliding direction D to push the two resilient arms 1193 of the flexible circuit board 119 to drive the circuit board 112, the surface mounted device 111, the lens assembly 113, the flexible auxiliary circuit board 119, the two light emitting components 11A, the cables 114 and the auxiliary cable 116 to slide together until the two light emitting components 11A abut against the two light guiding components 11C respectively.

Figure 8:
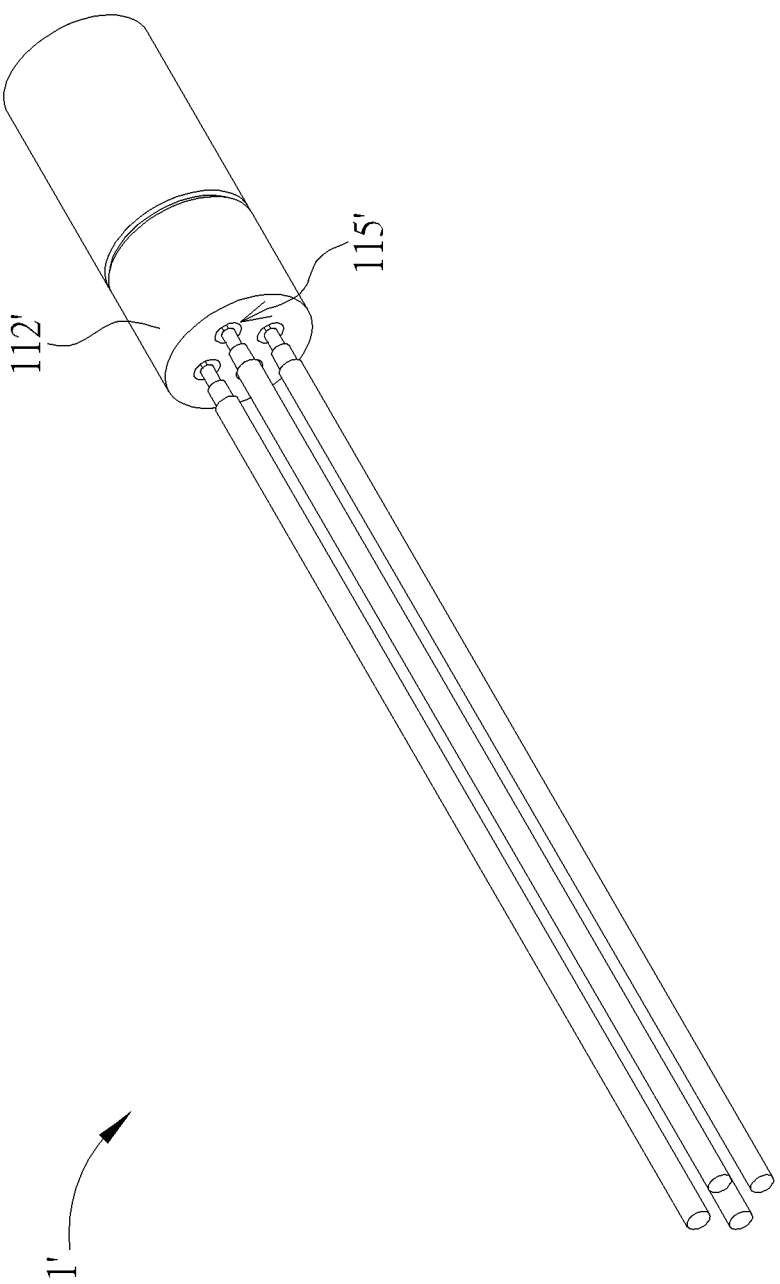
FIG. 8 is a partial diagram of an endoscope according to a second embodiment of the present invention.
Figure 9:
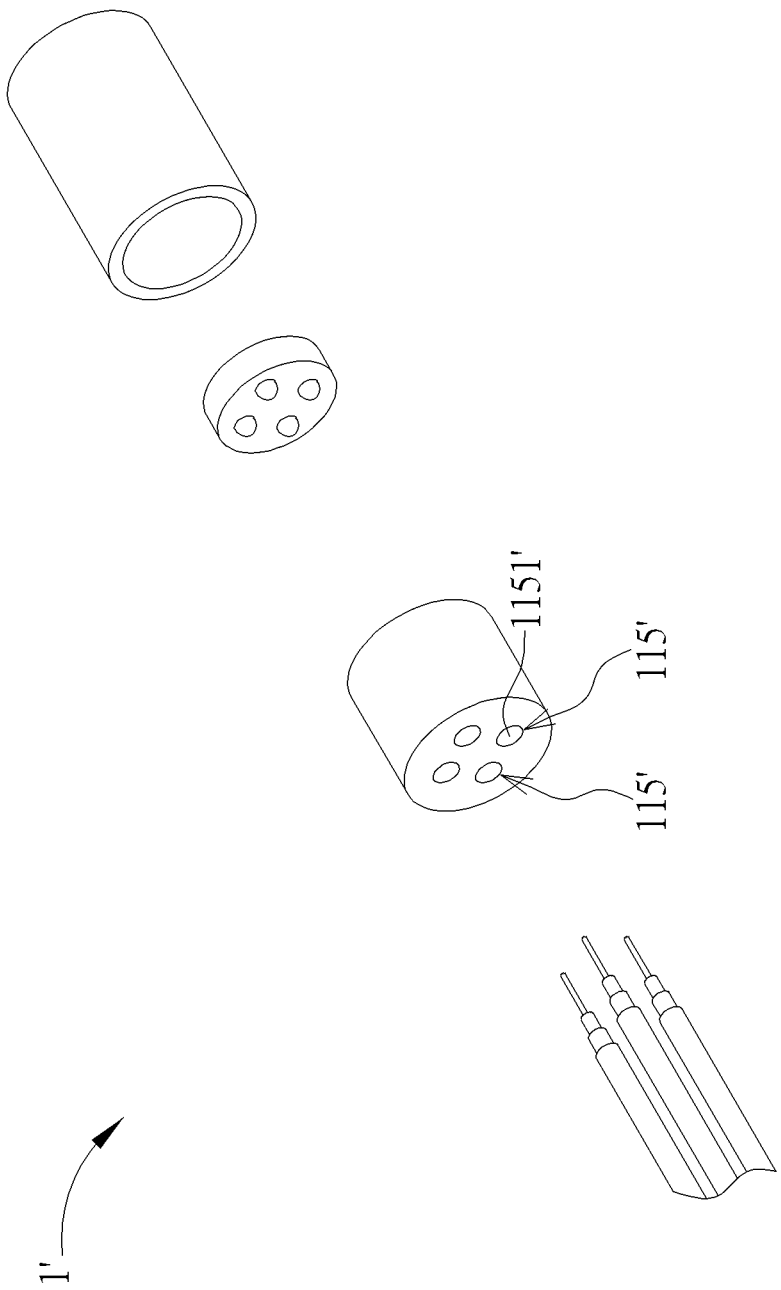
FIG. 9 and FIG. 10 are partial exploded diagrams of the endoscope according to the second embodiment of the present invention.
Figure 10:
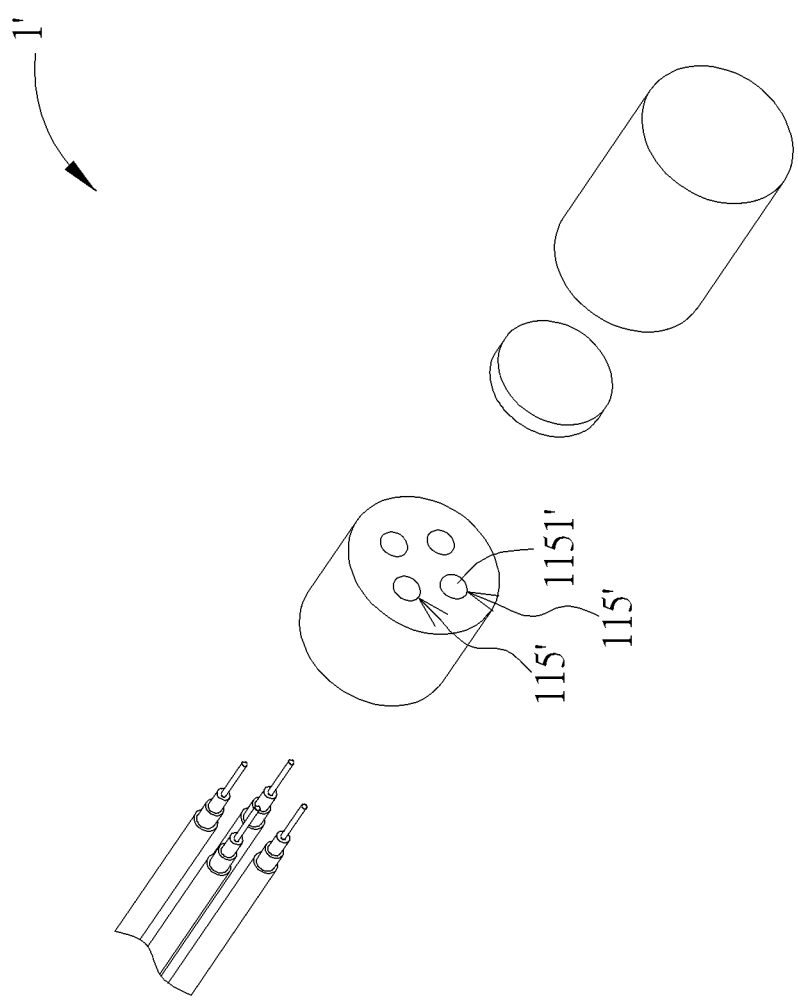

Please further refer to FIG. 8 to FIG. 10. FIG. 8 is a partial diagram of an endoscope 1' according to a second embodiment of the present invention. FIG. 9 and FIG. 10 are partial exploded diagrams of the endoscope 1' according to the second embodiment of the present invention. As shown in FIG. 8 to FIG. 10, different from the first embodiment, the endoscope 1' does not include the half through hole structure, the auxiliary cable, the flexible circuit board and the light emitting component. Understandably, in this embodiment, since there is no light emitting component and no flexible circuit board, the light guiding component and/or the mounting base also can be omitted, and a circuit board 112' can be a circular structure without any flat abutting structure. Furthermore, each of a plurality of conductive hole structures 115' includes a non-plated through hole 1151' without any ring-shaped pad portion and any plating inner wall and filled with the electrically conductive material. Other structures of this embodiment are similar to the ones of the first embodiment and can have similar variations described above. Detailed description for those structures and the related variations is omitted herein for simplicity.

Figure 11:
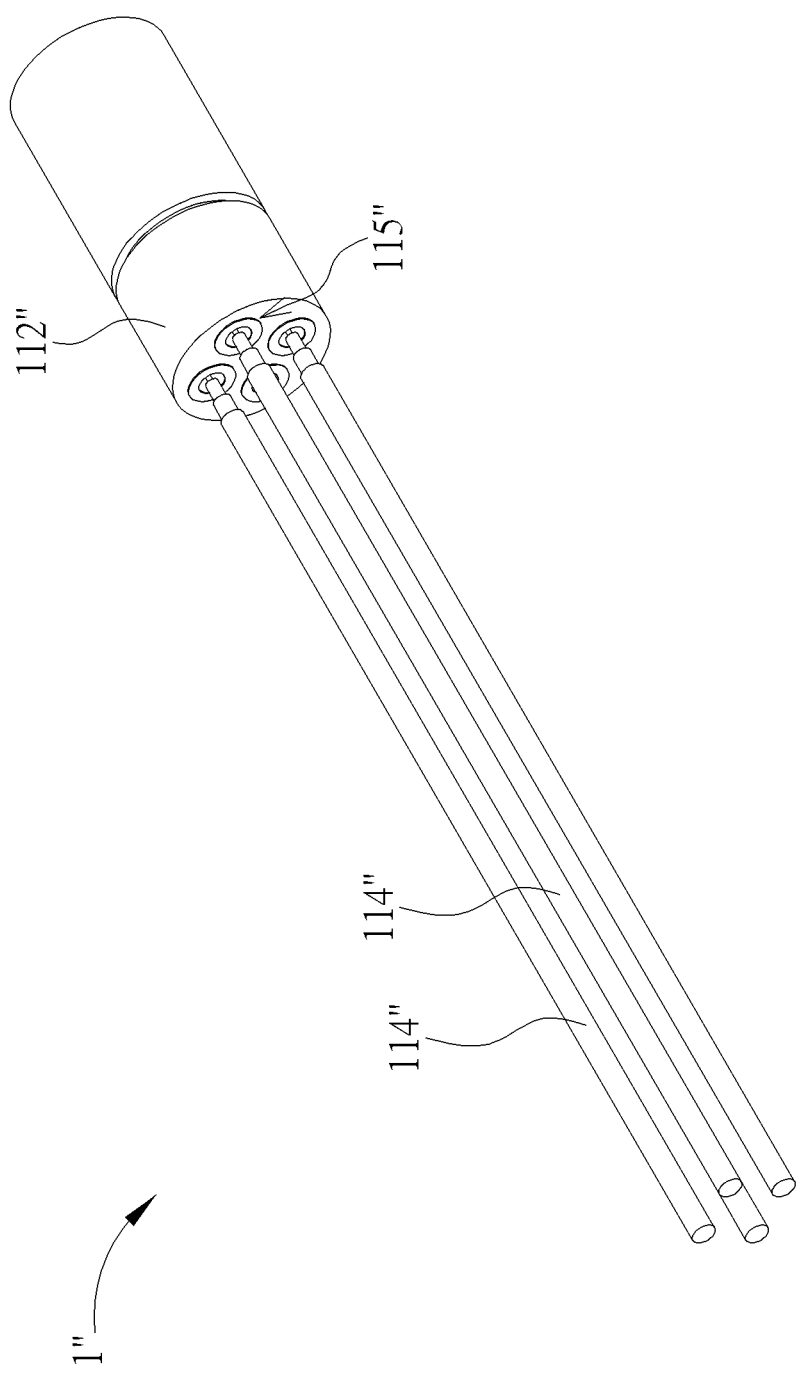
FIG. 11 is a partial diagram of an endoscope according to a third embodiment of the present invention.
Figure 12:
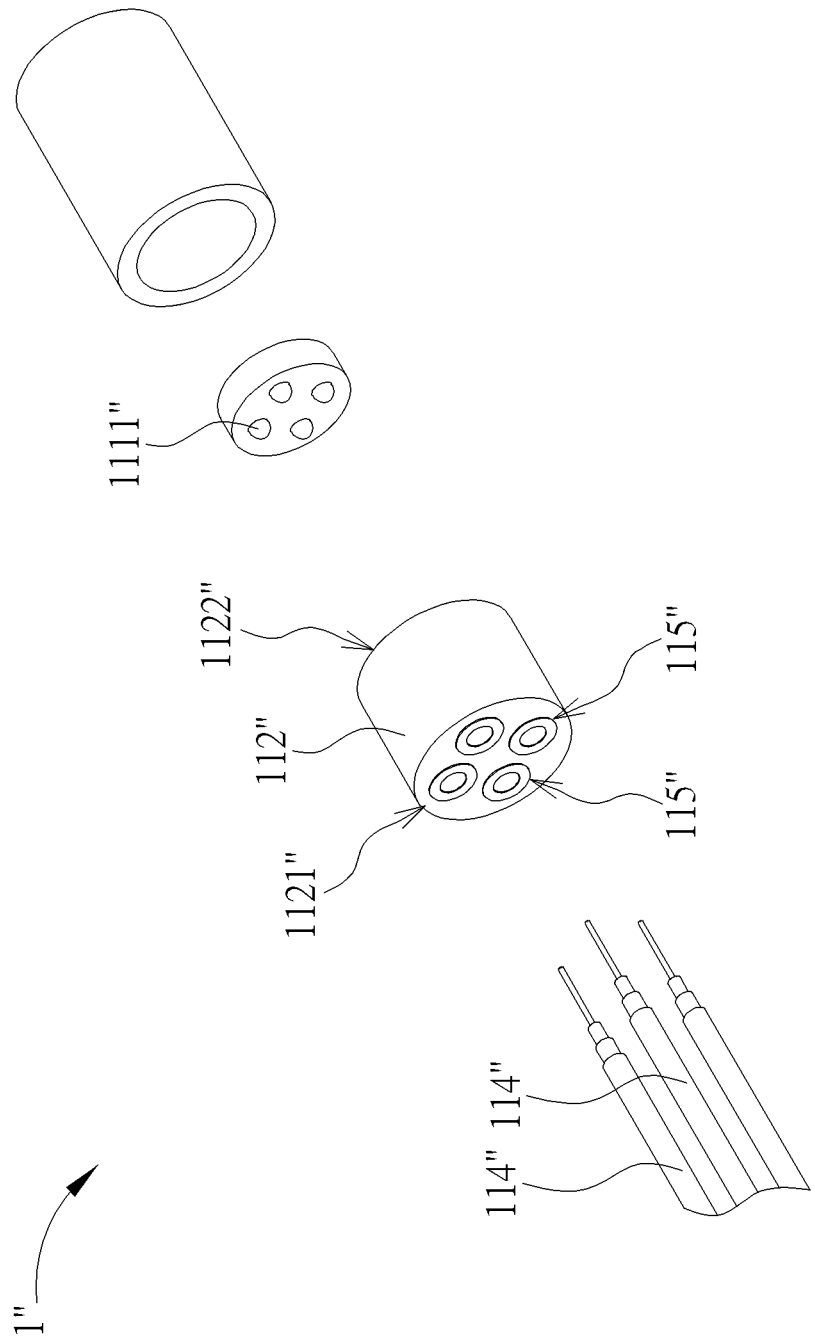
FIG. 12 and FIG. 13 are partial exploded diagrams of the endoscope according to the third embodiment of the present invention.
Figure 13:
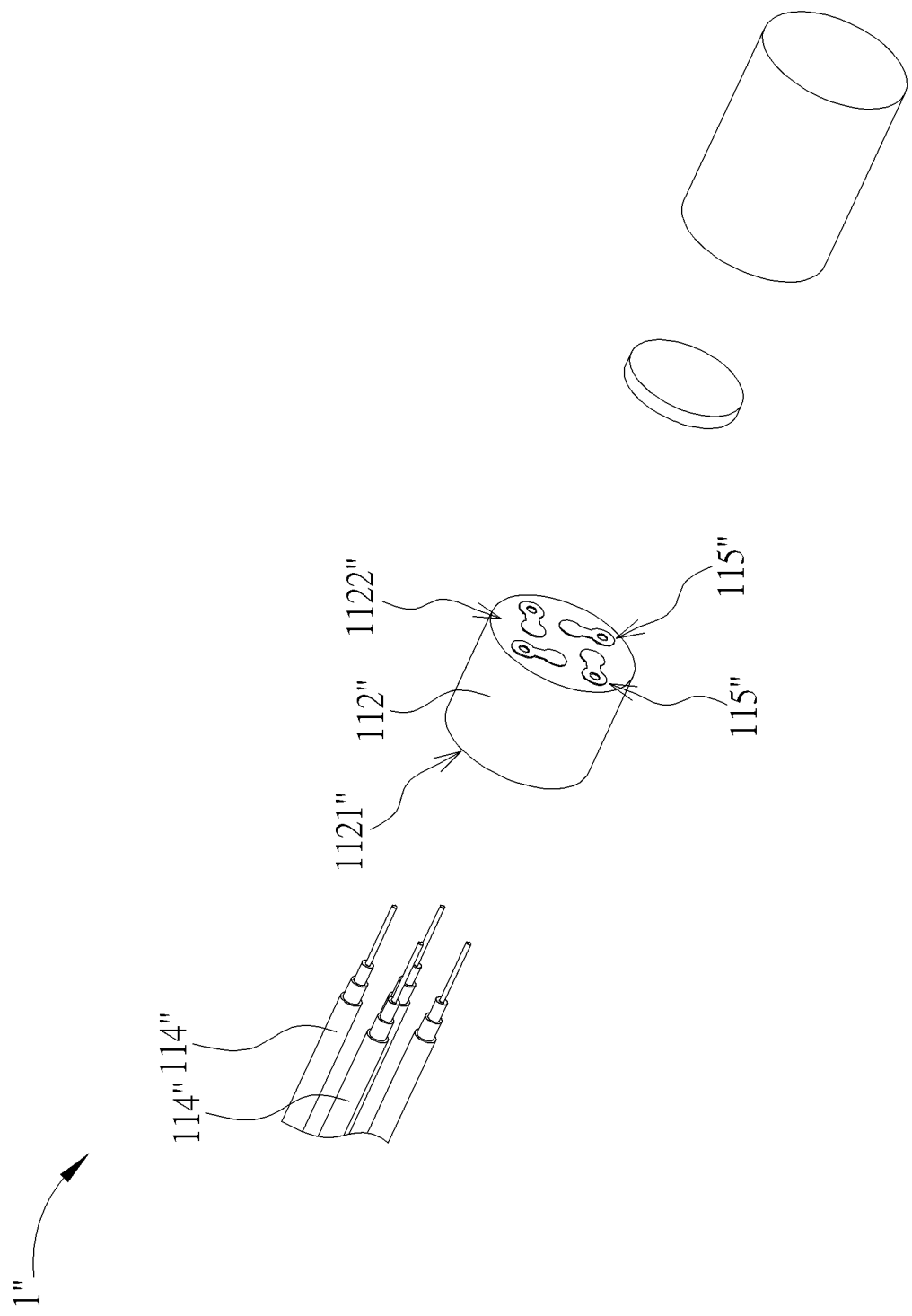
Figure 14:
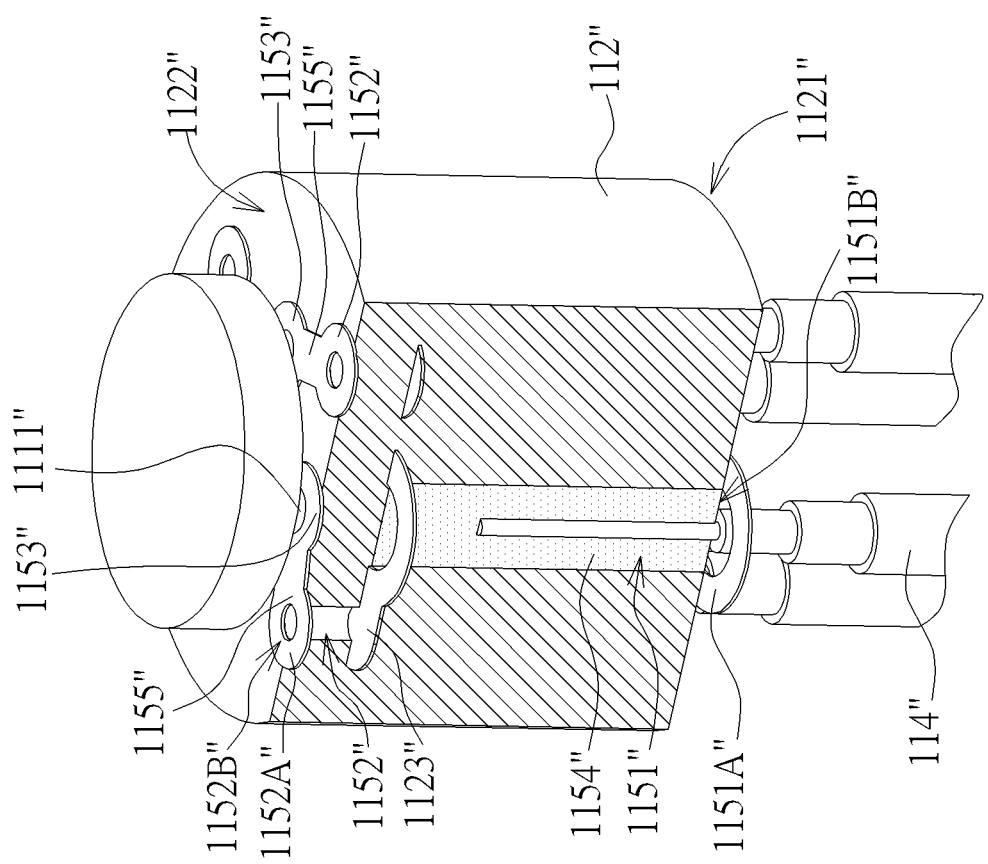
FIG. 14 is a partial internal diagram of the endoscope according to the third embodiment of the present invention.

Please further refer to FIG. 11 to FIG. 14. FIG. 11 is a partial diagram of an endoscope 1" according to a third embodiment of the present invention. FIG. 12 and FIG. 13 are partial exploded diagrams of the endoscope 1" according to the third embodiment of the present invention. FIG. 14 is a partial internal diagram of the endoscope 1" according to the third embodiment of the present invention. As shown in FIG. 11 to FIG. 14, different from the second embodiment, the circuit board 112" includes a first outer side 1121", a second outer side 1122" and a plurality of inner conductive layers 1123" disposed between the first outer side 1121" and the second outer side 1122". The first outer side 1121" and the second outer side 1122" of the circuit board 112" can be substantially perpendicular to an extending direction of each of cables 114". Each of a plurality of conductive hole structures 115" includes a first blind via hole 1151" with a first ring-shaped pad portion 1151A" located on the first outer side 1121" of the circuit board 112", a second blind via hole 1152" with a second ring-shaped pad portion 1152A" located on the second outer side 1122" of the circuit board 112", and a via contact 1153" located on the second outer side 1122" of the circuit board 112" and offset from the second ring-shaped pad portion 1152A". Each of the first blind via holes 1151" and the second via holes 1152" is provided with a plating inner wall electrically connected to the corresponding inner conductive layer 1123", so that each of the first blind via holes 1151" is electrically connected to the corresponding second blind via hole 1152" by the corresponding inner conductive layer 1123". Each of the first blind via holes 1151" has a first opening 1151B" formed on the first outer side 1121" of the circuit board 112" and surrounded by the corresponding first ring-shaped pad portion 1151A". Each of the second blind via holes 1152" has a second opening 1152B" formed on the second outer side 1122" of the circuit board 112" and surrounded by the corresponding second ring-shaped pad portion 1152A".

An extending direction of each of the first blind via holes 1151" is offset from an extending direction of the corresponding second blind via hole 1152". Each of a plurality of the cables 114" is inserted into the corresponding first blind via hole 1151" via the corresponding first opening 1151B" to locate a terminal of each of the cables 114" between the first outer side 1121" and the second outer side 1122" of the circuit board 112". Each of the first blind via holes 1151" is at least partially filled with an electrically conductive material 1154", so as to establish a mechanical and electrical connection of the terminal of the corresponding cable 114" and the corresponding first blind via holes 1151". Each of the via contacts 1153" is electrically connected to the corresponding second ring-shaped pad portion 1152A", e.g., by an outer conductive layer 1155". Each of a plurality of electrical connecting components 1111" is aligned with the corresponding via contact 1153" along the extending direction of the corresponding cable 114" and affixed with the corresponding via contact 1153" by soldering, so that each of the plurality of the electrical connecting components 1111" is electrically connected to the corresponding cable 114" by the corresponding via contact 1153", the corresponding outer conductive layer 1155", the corresponding second blind via hole 1152", the corresponding inner conductive layer 1123", the corresponding first blind via hole 1151" and the electrically conductive material 1154".

Furthermore, other structures of this embodiment are similar to the ones of the first embodiment and can have similar variations described above. Detailed description for those structures and the related variations is omitted herein for simplicity.

It should be noticed that in this embodiment, each of the first blind via holes 1151" is misaligned with the corresponding second blind via hole 1152" along an extending direction of the corresponding cable 114", and each of the electrical connecting components 1111" is misaligned with the corresponding cable 114" along the extending direction of the corresponding cable 114".

However, the present invention is not limited to this embodiment. For example, in another embodiment, the first outer side and the second outer side of the circuit board can be substantially inclined relative to the extending direction of each of the cables. Alternatively, in another embodiment, there can be only one via contact, one first blind via hole, one second blind via hole, one inner conductive layer, one cable and one electrical connecting component, and the via contact and the second ring-shaped pad portion of the second blind via hole can be integrally formed together and connected to each other directly or can be electrically connected to each other by a wire. Besides, the electrical connecting component can be aligned with the cable along the extending direction of the corresponding cable. Alternatively, in another embodiment, there can be no via contact, and both of the first blind via hole and the second blind via holes can be at least partially filled with the electrically conductive material. Besides, the electrical connecting component can be affixed with and electrically connected to the second ring-shaped pad portion of the second blind via hole and misaligned with the cable along the extending direction of the cable. Alternatively, in another embodiment, the endoscope can include structures similar to the ones of the third embodiment and further include the half through hole structure, the auxiliary cable, the flexible circuit board and the light emitting component of the first embodiment.

Moreover, it should be noticed that the surface mounted device can be an image sensing device used in any other image capturing apparatus, e.g., a microscope, or even can be any other device mounted by surface mounting technology used in any other apparatus. For example, the surface mounted assembly can be a printed circuit board assembly of a portable electronic device, e.g., a mobile phone a tablet computer or a laptop, and the surface mounted device can be a processor mounted on the printed circuit board assembly.

In contrast to the prior art, the present invention utilizes the conductive hole structure to be affixed with and electrically connected to the electrical connecting component of the surface mounted device and the terminal of the cable, so that the electrical connecting component of the surface mounted device can be electrically connected to the terminal of the cable by the conductive hole structure. The aforementioned configuration of the present invention is space-saving. Therefore, the present invention has advantages of compact structure and small size.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A surface mounted assembly comprising:
  a surface mounted device comprising at least one electrical connecting component;
  at least one cable; and
  a circuit board comprising a first outer side, a second outer side opposite to the first outer side, an inner conductive layer disposed between the first outer side and the second outer side and at least one conductive hole structure, the at least one conductive hole structure comprising a first blind via hole and a second blind via hole, the first blind via hole and the second blind via hole being electrically connected to the inner conductive layer, the first blind via hole having a first opening formed on the first outer side, the second blind via hole having a second opening formed on the second outer side, the at least one cable being inserted into the first blind via hole of the at least one conductive hole structure from the first outer side, a terminal of the at least one cable being located between the first outer side and the second outer side, the first blind via hole being at least partially filled with an electrically conductive material, wherein the surface mounted device is mounted on the second outer side of the circuit board, the terminal of the at least one cable and the at least one electrical connecting component of the surface mounted device are affixed with and electrically connected to the at least one conductive hole structure, and the surface mounted device is electrically connected to the at least one cable by the at least one conductive hole structure.

2. The surface mounted assembly of claim 1, wherein the first outer side and the second outer side of the circuit board are perpendicular to an extending direction of the at least one cable, the at least one electrical connecting component is aligned with the at least one cable along the extending direction of the at least one cable.

3. The surface mounted assembly of claim 1, wherein the at least one conductive hole structure further comprises at least one via contact located on the second outer side and offset from a pad portion of the second blind via hole surrounding the second opening, the at least one via contact is electrically connected to the pad portion of the second blind via hole, and the at least one electrical connecting component is aligned with the at least one via contact along the extending direction of the at least one cable and affixed with the at least one via contact.

4. The surface mounted assembly of claim 1, wherein the first blind via hole is misaligned with the second blind via hole along the extending direction of the at least one cable.

5. The surface mounted assembly of claim 1, wherein the first outer side and the second outer side of the circuit board are perpendicular to an extending direction of the at least one cable, the at least one electrical connecting component is misaligned with the at least one cable along the extending direction of the at least one cable.

6. An endoscope comprising:
  a surface mounted assembly comprising:
    a surface mounted device comprising at least one electrical connecting component and being an image sensing device;
    at least one cable; and
    a circuit board comprising a first outer side, a second outer side opposite to the first outer side, an inner conductive layer disposed between the first outer side and the second outer side and at least one conductive hole structure, the at least one conductive hole structure comprising a first blind via hole and a second blind via hole, the first blind via hole and the second blind via hole being electrically connected to the inner conductive layer, the first blind via hole having a first opening formed on the first outer side, the second blind via hole having a second opening formed on the second outer side, the at least one cable being inserted into the first blind via hole of the at least one conductive hole structure from the first outer side, a terminal of the at least one cable being located between the first outer side and the second outer side, the first blind via hole being at least partially filled with an electrically conductive material, wherein the surface mounted device is mounted on the second outer side of the circuit board, the terminal of the at least one cable and the at least one electrical connecting component of the surface mounted device are affixed with and electrically connected to the at least one conductive hole structure, and the surface mounted device is electrically connected to the at least one cable by the at least one conductive hole structure; and
  a lens assembly assembled with the surface mounted device.

7. The endoscope of claim 6, wherein the at least one conductive hole structure further comprises at least one via contact located on the second outer side and offset from a pad portion of the second blind via hole surrounding the second opening, the at least one via contact is electrically connected to the pad portion of the second blind via hole, and the at least one electrical connecting component is aligned with the at least one via contact along the extending direction of the at least one cable and affixed with the at least one via contact.

8. The endoscope of claim 6, wherein the surface mounted assembly further comprises at least one auxiliary cable, the circuit board further comprises a signal layer and a ground layer separated from the signal layer, at least one half through hole structure is formed on an outer periphery of the circuit board, the at least one half through hole structure has a first end portion adjacent to the first outer side of the circuit board and a second end portion adjacent to the second outer side of the circuit board, the signal layer and the ground layer are respectively located adjacent to the second end portion and the first end portion of the at least one half through hole structure, the at least one auxiliary cable is disposed inside the at least one half through hole structure, a terminal of the at least one auxiliary cable is affixed with and electrically connected to the signal layer, and a shield of the at least one auxiliary cable is affixed with and electrically connected to the ground layer.

9. The endoscope of claim 6, further comprising a flexible auxiliary circuit board, at least one light emitting component and at least one light guiding component, the flexible auxiliary circuit board is electrically connected to the circuit board, the at least one light emitting component is disposed on the flexible auxiliary circuit board and configured to emit light, and the at least one light guiding component is configured to guide the light emitted from the at least one light emitting component.

10. The endoscope of claim 6, further comprising at least one passive electronic component electrically connected to the circuit board.

11. The endoscope of claim 9, wherein the flexible auxiliary circuit board comprises a main body and at least one resilient arm extending from the main body, the at least one light emitting component is disposed on the at least one resilient arm, and the at least one light emitting component is biased to abut against the at least one light guiding component by the at least one resilient arm.

12. The endoscope of claim 9, wherein the circuit board comprises at least one auxiliary contact, the flexible auxiliary circuit board comprises at least one cooperating contact electrically connected to the at least one light emitting component, a portion of the at least one auxiliary contact is located on a lateral side of the circuit board, and the at least one cooperating contact is affixed with and electrically connected to the at least one auxiliary contact.

13. The endoscope of claim 10, wherein the circuit board comprises at least one auxiliary contact, the at least one passive electronic component comprises at least one cooperating contact, a portion of the at least one auxiliary contact is located on a lateral side of the circuit board, and the at least one cooperating contact is affixed with and electrically connected to the at least one auxiliary contact.

14. The endoscope of claim 12, wherein the portion of the at least one auxiliary contact and a portion of the at least one cooperating contact are perpendicular to each other.

* * * * *